United States Patent [19]
Kumar et al.

[11] Patent Number: 5,939,564
[45] Date of Patent: Aug. 17, 1999

[54] PROCESS OF LACTONIZATION IN THE PREPARATION OF STATINS

[75] Inventors: Yatendra Kumar; Rajesh Kumar Thaper, both of Haryana; S. M. Dileep Kumar, New Delhi; Jag Mohan Khanna, Haryana, all of India

[73] Assignee: Ranbaxy Laboratories Limited, New Delhi, India

[21] Appl. No.: 09/055,572

[22] Filed: Apr. 6, 1998

[30] Foreign Application Priority Data

Oct. 28, 1997 [IN] India ............................................ 3101

[51] Int. Cl.$^6$ ................................................. C07D 309/30
[52] U.S. Cl. ............................................................ 549/292
[58] Field of Search ................................... 560/254, 194; 549/292

[56] References Cited

U.S. PATENT DOCUMENTS 4,820,850  4/1989  Verhoeven et al. .
4,916,239  4/1990  Treiber .

*Primary Examiner*—Samuel Barts
*Attorney, Agent, or Firm*—Jayadeep R. Deshmukh

[57] ABSTRACT

A novel process of lactonizaton in the preparation of statins (e.g., the HMG—CoA reductase inhibitors lovastatin and simvastatin) employs very mild reaction conditions. The improved process comprises dissolving the open ring hydroxy acid form of the statins in an organic solvent by heating at a temperature, which ranges from ambient to reflux of the solvent, under anhydrous conditions to produce a solution, treating the solution with a mild catalyst at a temperature from about ambient to 50° C., and adding water to the solution to cause the statins in lactone form to crystalize from the reaction mixture. The mild catalyst used in the reaction is a salt of an organic base with an organic or inorganic acid, such as pyridine hydrobromide, pyridine hydrochloride, or pyridinium, p-toluene sulfonate. The organic solvent comprises a lower alkanol, a non-alcoholic polar solvent, or a mixture of the two.

10 Claims, No Drawings

PROCESS OF LACTONIZATION IN THE PREPARATION OF STATINS

BACKGROUND OF THE INVENTION

Lovastatin and its analogs, e.g., simvastatin, are potent antihyper-cholesterolemic agents that function by limiting cholesterol biosynthesis by inhibiting the enzyme HMG—CoA reductase. These compounds, which may be referred to generally as statins, are known to exist in open ring hydroxy acid and also in lactone form. The lactone form and the hydroxy acid form of these compounds have the following general structural Formulas:

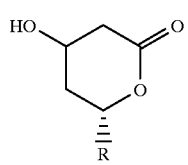

(I)

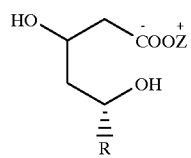

(II)

wherein Z is hydrogen, a metal cation, such as sodium or potassium, or $NH_4$, and R is

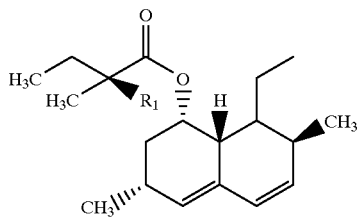

wherein $R_1$ is H or $CH_3$.

The open hydroxy acid form of the statins (Formula II) is the one which is biologically active. However, the statins are generally administered to a patient in the lactone form (Formula I), which is converted to its active metabolite, the hydroxy acid form, in the body.

In the process of manufacture of lovastatin and its analogs, e.g., simvastatin, the lactonization of free hydroxy acid or its salt to lactone form constitutes an essential step.

Processes known in the literature for the lactonization of the free hydroxy acid or its salts are either carried out under drastic heat conditions, i.e., refluxing with inert solvents, or catalyzed by strong acids when lactonization is effected at ambient temperature. The process disclosed in U.S. Pat. No. 4,820,850 involves heating the free acid or its salt, e.g., the ammonium salt, to reflux temperature (usually 100–110° C.) in high boiling hydrocarbon solvents such as toluene for 7–8 hours. The ambient acidity of the acid is believed to be responsible for the lactonization reaction at these high temperatures. In addition, water which is formed as a by-product of the reaction is continuously removed by azeotropic distillation, which forces the reaction to near completion. The process of lactonization under heat conditions of reflux temperatures is complicated by the formation of many impurities, of which dimer formation especially lowers the quality of the final lactone product. The dimer is a difficult-to-remove impurity and is present at the levels of 0.4 to 0.8% in the product. In order to minimize the dimer impurity, high dilutions are often used in the lactonization reaction at the cost of the efficiency of the reaction and of the process, which is disadvantageous at a commercial manufacturing scale.

U.S. Pat. No. 4,916,239 discloses another process wherein the lactonization reaction is carried out at room temperature by treating the free hydroxy acid ammonium salt of a mevinic acid in a mixture of acetic acid and water, and in the presence of a strong acid catalyst. After the free hydroxy acid-lactone equilibrium is established (reaction has proceeded to 50% conversion), water is gradually added in lots to effect crystallization of the lactone from the reaction medium. This removal of lactone continuously shifts the equilibrium to the lactone side thus leading to reaction completion. This process suffers from several disadvantages and is also not convenient to operate at a large scale for a variety of reasons, some of which are discussed below Use of a strong mineral or an organic acid catalyst, e.g., formic, phosphoric, trifluoroacetic, sulphuric, hydrochloric, p-toluene sulphonic, methanesulphonic acids, etc., in quantities varying from 1.2 to 1.5 molar equivalents makes this process hazardous and environmentally unacceptable on an industrial scale. The excess acid catalyst which is used needs to be neutralized by adding a strong base before filtration of the product.

Furthermore, the lactonization reaction is only about 50% complete after the equilibrium is achieved. At this point in time, any fast or premature addition of water can lead to serious crystallization and filtration problems. Moreover, reaction and subsequent workup takes about 9–12 hours for completion, thereby decreasing the efficiency of the process.

The above-mentioned disadvantages make the process of U.S. Pat. No. 4,916,239 operationally tedious, inefficient, expensive and environmentally hazardous on an industrial scale.

SUMMARY AND DETAILED DESCRIPTION OF THE INVENTION

The aim of the present invention is to provide an efficient method for lactonization of statins which method avoids the use of strong corrosive acids and drastic heat conditions and gives a lactonized product of high purity and yield.

The present invention provides a novel process for converting the HMG—CoA reductase inhibitors, e.g., the open hydroxy acid forms of lovastatin, simvastatin, and analogs thereof, into their lactone forms, and is convenient to operate on an industrial scale. It allows the lactonization reaction to proceed at moderate temperatures without the use of industrially unsafe strong acids.

Specifically, the process of the present invention comprises dissolving the open hydroxy acid in its salt form (II), preferably the ammonium salt, by heating in an organic solvent at a temperature from about ambient to reflux of the solvent under anhydrous conditions, treating with a mild catalyst, as hereinafter described, at a temperature from about ambient to 50° C., precipitating the lactonized product by the addition of water and collecting the crystalline product (I) from the mixture. The reaction can be represented as follows:

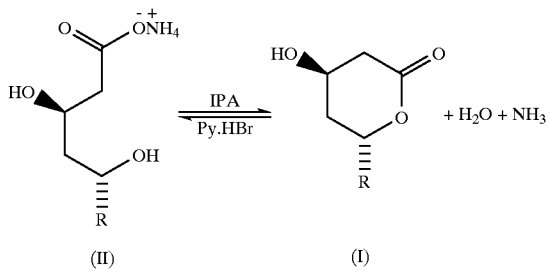

wherein R is:

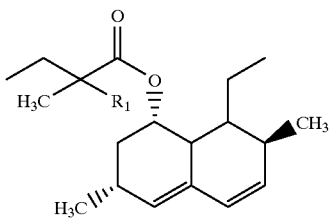

wherein $R_1$=H or $CH_3$.

The mild catalysts to be used in the instant invention are the salts of organic bases with inorganic or organic acids, such as pyridine hydrobromide, pyridine hydrochloride, or pyridine p-toluene sulfonate. Most preferably, pyridine hydrobromide is used. The catalysts are used in small catalytic quantities ranging from 0.1 to 0.5 molar equivalents, preferably ranging from 0.1 to 0.25. The term "organic solvent" in this invention refers to any lower alkanol or non-alcoholic polar solvent. The lower alkanol includes those primary, secondary and tertiary alcohols having from one to six carbon atoms. Suitable lower alcohol solvents also include methyl, ethyl, n-propyl, n-butyl, isobutyl and t-butyl alcohols. Preferably, the lower alkanol solvent used in the present invention will be methyl alcohol, isopropyl alcohol or isobutyl alcohol. Most preferably, isopropyl alcohol is used.

The non-alcoholic polar solvents which may be used as the organic solvent in this invention include acetone, methyl ethyl ketone, 2-butanone, 4-methylpentan-2-one, tetrahydrofuran or acetonitrile. Mixtures of two or more lower alkanols and/or other non-alcoholic solvents can also be used.

The lactonization reaction is efficiently accomplished within about 1–2 hours. However, the length of time required will vary depending on such factors as temperature of reaction, concentration and presence or absence of stirring.

The amount of solvent is at least 1 part by volume per part of the starting material. Higher amounts of solvents and generally up to 30 parts by volume may be used. Amounts higher than 30 volumes are not useful from an economic point of view because large size reactors would be necessary.

The product obtained under the above defined conditions is highly crystalline and is easily filterable. The product is very pure (>98% HPLC purity) with much less formation of impurities as compared to the prior art procedures. It does not require further purification. Furthermore, the process is safe and environment friendly as very mild catalysts and non-drastic conditions are employed which are convenient for operation at a commercial scale.

The present invention is illustrated by the following specific examples which are not intended to limit the effective scope of the claims.

EXAMPLE-1

Preparation of 6(R)-[2-[8(S)-(2,2-dimethylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one. (Formula (I), $R_1$=$CH_3$).

Ammonium-7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoate (Formula II, $R_1$=$CH_3$), (10 g, 98% pure, 0.022 moles) was suspended in isopropyl alcohol (300 ml) and refluxed for 1 hour at 81–82° C. The volume of the solvent was reduced to about half by distillation during this period to give a clear solution, which was cooled to 45° C. Dry pyridine hydrobromide (0.33 g, 0.002 moles) was added under nitrogen atmosphere and the mixture was stirred at 42–45° C. for about two hours. Reaction was monitored on TLC.

After the reaction was complete, water (160 ml) was added and the reaction mixture was stirred for 5 minutes. More water (160 ml) was then added slowly to crystallize out the lactonized product. The slurry was further stirred for one hour at 30–35° C. and then at 15–18° C. for 30 minutes. Filtration followed by washing with water (15 ml×3) and drying under vacuum afforded the title product (8.4 g) in >91% yield in pure crystalline form. Purity by HPLC>98%.

EXAMPLE-2

Preparation of 6(R)-[2-[8(S)-(2-methylbutyryloxy)-2(S),6(R)-dimethyl-1,2,6,7,8a(R)-hexahydronaphthyl-1(S)]-ethyl]-4(R)-hydroxy-3,4,5,6-tetrahydro-2H-pyran-2-one. (Formula (I), $R_1$=H).

Ammonium-7-[1,2,6,7,8a(R)-hexahydro-2(S),6(R)-dimethyl-8(S)-(2-methylbutyryloxy)-1(S)naphthyl]-3(R),5(R)-dihydroxyheptanoate (Formula II, $R_1$=H) (30 g, 75% assay, 0.0512 moles equivalent) was suspended in isopropyl alcohol (600 ml) and refluxed at 81–82° C. for 2 hours. The volume of the solvent was reduced to about 300 ml by distillation during this period. To the clear solution thus obtained, was added catalyst, pyridine hydrobromide (2 g dry, 0.0125 moles) under nitrogen atmosphere at 50° C. The contents were further stirred at 40–45° C. for about 2 hours when the reaction was complete. Water (150 ml) was added over 10 minutes followed by stirring for 5 minutes. More water (50 ml) was added to crystallize out the lactonized product completely. Filtration, washing by water (20 ml×2) and drying in vacuo at 40–42° C. afforded the title compound as a white crystalline material (22 g, 90% assay, 95.6% yield). Purity by HPLC=98.70%.

EXAMPLE-3

Preparation of 6(R)-[2-[8(S)-(2,2-dimethylbutyryloxy)-2(S),6(R)-dimethyl-1,2,6,7,8,8a(R)hexahydronaphthyl-1(S)]-ethyl]-4(R)-hydroxy-3,4,5,6-tetrahydro-2H-pyran-2-one. (Formula (I), $R_1$=$CH_3$).

Adopting the same procedure as described in Example -1 and substituting pyridine hydrochloride as catalyst, the title compound was obtained in >98% purity and 89.75% yield.

EXAMPLE-4

Preparation of 6(R)-[2-[8(S)-(2-methylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one. ( (Formula (I), $R_1$=H)

Following the procedure substantially as described in Example -2 and substituting pyridine hydrochloride, the title compound was prepared in over 98% yield and >97% purity.

EXAMPLE-5

Preparation of 6(R)-[2-[8(S)-(2-methylbutyryloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one. (Formula (I), R₁=H)

Following the procedure substantially as described in Example -2 and substituting pyridinium p-toluene sulphonate as catalyst, the title compound was obtained in over 96% yield and 98.7% purity.

We claim:

1. A process for the manufacture of a compound of Formula I:

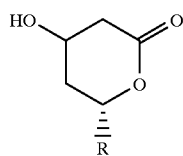
(I)

wherein R is:

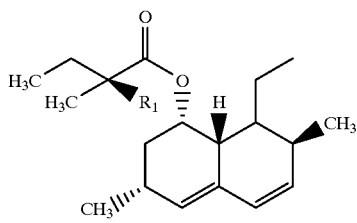

wherein $R_1$ is H or $CH_3$, which comprises dissolving a compound of Formula II:

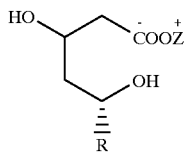
(II)

wherein Z is hydrogen, a metal cation, or $NH_4$, and wherein R is as defined above, in an organic solvent by heating at a temperature from about ambient to reflux of said solvent under anhydrous conditions to obtain a solution, treating the solution with a mild catalyst at a temperature from about ambient to about 50° C., and adding water to the solution thereby causing the precipitation of the compound of Formula I.

2. The process of claim 1 further comprising collecting the compound of Formula I as a crystalline product.

3. The process of claim 1 wherein said mild catalyst is a salt of an organic base with an inorganic or an organic acid.

4. The process of claim 1 wherein said mild catalyst is pyridine hydrobromide, pyridine hydrochloride, or pyridinium p-toluene sulfonate.

5. The process of claim 1 wherein said organic solvent comprises a lower alkanol having 1 to 6 carbon atoms.

6. The process of claim 5 wherein said lower alkanol comprises a primary, secondary, or tertiary alcohol.

7. The process according to claim 5 wherein said lower alkanol comprises methyl alcohol, ethyl alcohol, isopropyl alcohol, n-propyl alcohol, n-butyl alcohol, isobutyl alcohol, or t-butyl alcohol.

8. The process of claim 1 wherein said solvent is a non-alcoholic polar solvent.

9. The process of claim 8 wherein said non-alcoholic polar solvent comprises acetone, methyl ethyl ketone, 4-methyl pentan-2-one, tetrahydrofuran, or acetonitrile.

10. The process of claim 1 wherein said organic solvent is a mixture of a lower alkanol and a non-alcoholic polar solvent.

* * * * *